United States Patent
Kim et al.

(10) Patent No.: US 6,205,349 B1
(45) Date of Patent: *Mar. 20, 2001

(54) DIFFERENTIATING NORMAL LIVING MYOCARDIAL TISSUE, INJURED LIVING MYOCARDIAL TISSUE, AND INFARCTED MYOCARDIAL TISSUE IN VIVO USING MAGNETIC RESONANCE IMAGING

(75) Inventors: Raymond Kim, Chicago; Robert M. Judd, Wheeling; Jeffrey M. Bundy; Orlando P. Simonetti, both of Naperville, all of IL (US)

(73) Assignees: Siemens Medical Systems, Inc., Iselin, NJ (US); Northwestern University, Evanston, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,548
(22) Filed: Sep. 29, 1998
(51) Int. Cl.[7] ................................. A61B 5/055
(52) U.S. Cl. ............................................. 600/420
(58) Field of Search .................. 600/420, 410; 424/9.3, 9.323

(56) References Cited

U.S. PATENT DOCUMENTS

| | | | |
|---|---|---|---|
| 4,859,450 | * 8/1989 | Khaw et al. | 600/420 |
| 5,111,820 | * 5/1992 | Axel et al. | 600/410 |
| 5,377,681 | * 1/1995 | Drane | 600/420 |
| 5,387,410 | * 2/1995 | Bosworth et al. | 600/420 |
| 5,492,814 | * 2/1996 | Weissleder | 600/420 |
| 5,910,112 | * 6/1999 | Judd et al. | 600/410 |

OTHER PUBLICATIONS

Peter Reimer, MD; Ralph Wiessleder, MD, PhD; Jack Wittenberg, MD; Thomas J. Brady, MD, "Receptor-directed Contrast Agents for MR Imaging: Preclinincal Evaluation with Affinity Assays" *Radiology* 1992; 182: 565–569.

I. Kofi Adzamli; Monte Blau; Marc A. Pfeffer; Michael A. Davis, "Phosphonate–Modified Gd–DTPA Complexes. III: The Detection of Myocardial Infarction by MRI" MRM 29:505–511 (1993).

* cited by examiner

*Primary Examiner*—Ruth S. Smith
(74) *Attorney, Agent, or Firm*—Mark H. Jay

(57) ABSTRACT

By administering MR contrast agent such as Gd-DPTA, waiting for a predetermined period of time and then acquiring T1-weighted MR image data, infarcted myocardial tissue can be distinguished from injured myocardial tissue. An in vivo cine MR study is used to distinguish normal myocardial tissue from injured or infarcted myocardial tissue. As a result, it is possible to distinguish between normal, injured but living, and infarcted myocardium using MR imaging.

8 Claims, 1 Drawing Sheet

DIFFERENTIATING NORMAL LIVING MYOCARDIAL TISSUE, INJURED LIVING MYOCARDIAL TISSUE, AND INFARCTED MYOCARDIAL TISSUE IN VIVO USING MAGNETIC RESONANCE IMAGING

BACKGROUND OF THE INVENTION

The invention relates to cardiology, and more particularly relates to diagnosis of diseases of the myocardium. In its most immediate sense, the invention relates to diagnosis of myocardial disease using magnetic resonance imaging (MRI).

Physicians recognize three distinct categories in which myocardial tissue may be classified. One of these is "normal". "Normal" myocardial tissue is living tissue that is capable of normal movement during the normal expansion and contraction of the heart during the cardiac cycle. For the purposes of this patent application, the determination whether myocardial tissue is normal is made when the patient is at rest.

Another category of myocardial tissue is "injured" tissue that does not move normally during the cardiac cycle. This category includes tissue that is poorly perfused ("ischemic"), and also includes tissue that may be "stunned" and temporarily dysfunctional as a result of an earlier ischemic event.

Finally, myocardial tissue can be categorized as "infarcted". Infarcted tissue is dead. It cannot be treated or brought to life again. As used herein, "infarcted" myocardium includes acutely necrotic myocardium and scar tissue that eventually replaces acutely necrotic myocardium.

When a physician has diagnosed a patient as having ischemic heart disease, it is important to know whether the myocardium is injured or infarcted, and where. Once the existence and extent of injury and/or infarction has been determined, the physician can decide whether e.g. to treat the patient with drugs or whether to carry out a surgical intervention.

Physicians often use myocardial radionuclide studies to help make this determination. A myocardial radionuclide study is a technique whereby the patient's blood is radiolabelled using a radioisotope of a type that is taken up by myocardial tissue (e.g. Thallium). The patient's heart is then imaged using a scintillation camera in a nuclear medicine or positron emission tomography ("PET") study. If a particular region of the myocardium takes up the radioisotope, that region is assumed to contain living tissue; if not, the region is assumed to contain infarcted tissue. However, because both perfusion and viability are necessary for uptake, it may be difficult to distinguish the relative contributions that ischemia and infarction make to the defect.

Nuclear medicine studies also have very poor spatial resolution. As a result, such studies do not precisely show where tissue is dead, where tissue is injured, and where tissue is normal. Furthermore, nuclear medicine studies may take a long time (a conventional multi-scan myocardial radionuclide study may require five hours or more including the time between scans). MRI studies, on the other hand, have excellent spatial resolution and can be completed quickly (in, e.g., less than one hour), but such studies have not heretofore been able to distinguish between normal, injured, and infarcted myocardial tissue.

It would be advantageous to provide a methodology that would permit a physician to distinguish between normal, injured, and infarcted myocardial tissue, with a high degree of spatial resolution.

It would also be advantageous to provide a methodology that would permit such a distinction to be drawn in a study of relatively short duration.

It is therefore one object of the invention to provide methodology whereby a physician can identify infarcted myocardial tissue with a high degree of spatial resolution.

Another object is to provide methodology to distinguish between normal, injured, and infarcted myocardial tissue using a study having a comparatively rapid duration.

Another object is, in general, to improve on known methodology of this general type.

The invention proceeds from a discovery that Gadolinium (Gd) based MR contrast agents (such as Gd-DTPA, which is a chelate of Gadolinium that is known to be an untargeted MR contrast agent preferentially hyperenhance infarcted myocardial tissue after the passage of a predetermined interval of time (advantageously, between approximately 10 and 90 minutes). Although the mechanism for this is not yet precisely known, it is likely that the contrast agent does not enter living myocardial cells, but does enter dead myocardial cells via broken cell membranes. In the case of scar tissue, it may be that the contrast agent accumulates in the increased extracellular space of the collagen matrix. As a result, the precise location of infarcted tissue can be visualized in an MR image acquired e.g. 10 to 90 minutes after administration of the contrast agent; dead tissue will appear hyperenhanced in the image, while normal and injured tissue will not. In short, the invention proceeds from the realization that after a predetermined waiting period, myocardial regions hyperenhanced with MR contrast agent are exclusively dead. Thus, as a result of this discovery, infarcted tissue can be precisely localized using MRI, faster and with higher spatial resolution than a nuclear medicine study.

It should be noted that such a hyperenhanced region occasionally has an unenhanced subregion at its center. This unenhanced subregion is also infarcted and it only shows up as unenhanced because the contrast agent has not reached it at the time the MR study has been carried out.

Advantageously, and in accordance with the preferred embodiment, a T1-weighted MR pulse sequence (specifically a segmented T1-weighted inversion recovery turboFLASH implementation) is used to produce a T1-weighted MR image of the patient's heart. This makes the location of the contrast agent particularly apparent and makes it easier to identify infarcted tissue.

Once it is possible to identify infarcted tissue, it is then possible to distinguish between normal tissue and injured tissue even though both enhance identically in the MR image. This distinction can be drawn by using a cine MR study to determine regions of the myocardium that do not move normally during the cardiac cycle. If an abnormally moving region is hyperenhanced by contrast agent, the region is infarcted; if the abnormally moving region is not hyperenhanced, the region is injured. Normally moving regions indicate normal tissue.

BRIEF DESCRIPTION OF THE DRAWING

The invention will be better understood with reference to the accompanying exemplary and non-limiting drawing, which shows a flow chart of a preferred embodiment of the invention.

DETAILED DESCRIPTION OF PREFERRED EMBODIMENTS

Figure 1:
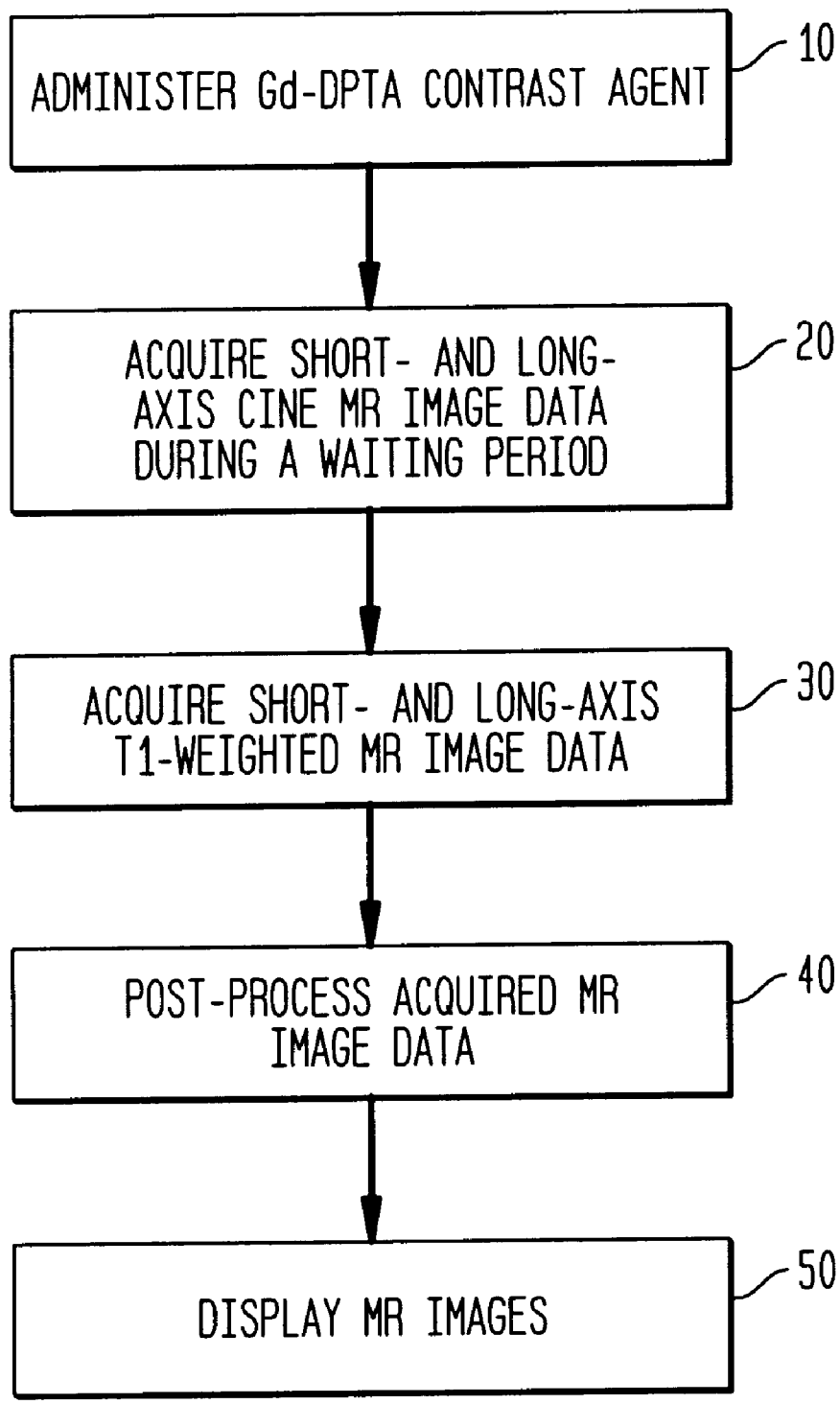

The herein-described medical phenomena are based upon experiments conducted on dogs. However, it is believed that the dog model provides a reasonable scientific basis upon which to believe that the herein-described invention is applicable to human beings and not merely to dogs; results in human subjects thus far are consistent with this belief.

In these experiments, the dogs were subjected to surgery to produce two different types of cardiac injuries: transient ischemia and infarction. In one type, one of the dog's coronary arteries was temporarily occluded by a hydraulic occluder and thereby caused to become seriously (but reversibly) ischemic. In the other type of injury, another one of the dog's cardiac arteries was sewed shut, producing an infarct. The dogs were injected with Gd-DPTA and imaged in vivo using an MR imager. Thereafter, the dogs were sacrificed and dissected, permitting pathological findings to be compared with the MR images.

These experiments demonstrated that after a delay of 30 to 60 minutes from administration of Gd-DPTA, only regions of infarcted myocardial tissue were hyperenhanced in the MR image. Normal tissue and transiently ischemic tissue were not hyperenhanced; those regions shown as hyperenhanced in the MR image corresponded exactly to regions that were shown on pathology study to be infarcted. Furthermore, transiently ischemic regions showed no hyperenhancement even when the ischemia was prolonged to the maximum duration beyond which cell death is known to occur (15 minutes in dog).

The hyperenhancement that occurs in infarcted myocardium also appears in myocardial scar tissue. In the above-referenced experiments on dogs, the animals were imaged in vivo at 8 weeks. The infarcts hyperenhanced at that time. Histology confirmed scar at the hyperenhanced region and the size of the hyperenhanced region in the MR image was identical to the size of the scar by histology.

It has long been known that a cine MR study, which produces a cardiac-gated series of images showing cardiac motion during the cardiac cycle, can be used to identify non-normal regions of the myocardium. This is because injured and infarcted regions of the myocardium are not capable of contracting, and do not move normally during expansions and contractions of the chambers of the heart. It is therefore possible to identify those non-normal myocardial regions that are either injured or infarcted. If a particular region shows as abnormal in a cine MR study and is not hyperenhanced after a delay of e.g. 30 minutes after administration of Gd-DTPA, the region is injured (ischemic or stunned). If a particular region shows as abnormal in a cine MR study and is hyperenhanced after a delay of e.g. 30 minutes after administration of Gd-DTPA, the region is infarcted.

Advantageously, the MR study is carried out by producing a T1-weighted MR image. This makes optimum use of the currently available Gd-based contrast agents and makes hyperenhancement particularly apparent in the MR image. Suitable T1-weighted MR pulse sequences are a) magnetization driven spoiled gradient acquisitions in the steady state ("MD-SPGR" sequences) and b) inversion-recovery fast low-angle shot pulse sequences ("IR-FLASH" sequences). Typical parameters were as follows:

MD-SPGR sequences:
TE=2 ms
TR=6 ms
Voxel Size: 1×1×6 mm
k-space data segmented over 3 cardiac cycles (33 lines/cycle)
4 averages for each line of k-space data
60 dummy RF pulses prior to acquisition of MR image data IR-FLASH sequences:
TE=2 ms
TR=6 ms
Inversion Delay=300 ms
Voxel Size: 1×1×6 mm
k-space data segmented over 4 cardiac cycles (33 lines/cycle)
MR image data acquired every other cardiac cycle to allow T1 relaxation In principle, it does not matter whether the acquisition of cine MR data precedes or follows the administration of MR contrast agent. It may be advantageous to perform the cine imaging first, immediately following injection of the contrast agent. This makes use of the waiting period required after the administration of the contrast agent and avoids the need to prolong the study (and to thereby reduce patient throughput through the MR imager)

In the preferred embodiment, the waiting period is at least about 10 minutes and at most about 90 minutes, and is advantageously about 30 minutes. These periods of time are not required; they are chosen for convenience. It may alternatively be possible for the wait period to be less than 10 minutes or more than 90 minutes.

In the preferred embodiment, the cine MR acquisition is taken along the long and short axes of the left ventricle. This is not necessary, but is convenient because a commercially available software package (ARGUS, from Siemens AG, of Erlangen, Germany) was used to quantify myocardial wall motion. As compared with an estimation of wall motion carried out by visual inspection, the use of ARGUS software provides a more objective manner of assessing abnormalities in local and regional wall motion. The manner in which the cine MR data are acquired is not part of the invention, and other acquisition methodologies can be used instead. In addition, wall motion need not necessarily be assessed using ARGUS software or any other quantitative techniques.

There are various ways in which the various MR images can be displayed. The manner in which MR image data is displayed is not a part of this invention.

In the preferred embodiment, T1-weighted MR image data are acquired using the empirically-measured inversion time of the patient's heart. (The inversion time is the time between an RF inversion pulse and an MR data acquisition in which the normal myocardium appears black.) This aligns the centerline of the k-space matrix with the null point of the patient's normal myocardium. By doing this, the acquisition produces an image with optimal contrast characteristics. However, this is not required; suboptimal data may be sufficient for most diagnostic purposes.

Hence, in accordance with the preferred embodiment of the invention, in step 10, Gd-DPTA MR contrast agent is administered in a living patient. Then, to make use of the necessary waiting time, multiple short- and long-axis cine MR data acquisitions are carried out in step 20. After completing the cine acquisitions, the inversion time required to null the signal from normal myocardium is empirically determined by using a series of T1-weighted MR data acquisitions.

Once this inversion time is known, short- and long-axis T1-weighted MR image data are acquired from the patient's heart in step 30. In the preferred embodiment, this is done by gating the RF inversion pulse to the patient's ECG signal, waiting the empirically determined inversion time, and then acquiring some or all the lines of MR image data. If image acquisition is carried out by segmenting the k-space matrix, the application of RF-gated inversion pulses, the waiting for the empirically-determined inversion time and the acquisition of the MR image data is repeated until the entire k-space matrix has been filled with lines of data. If image acquisition is carried out in a single-shot fashion, all the lines of MR image data are acquired following a single RF-gated inversion pulse.

After all this MR data acquisition has been completed, the MR image data are post-processed in step 40 and then displayed in step 50. Although one or more preferred embodiments have been described above, the scope of the invention is limited only by the following claims.

What is claimed is:

1. A method of identifying infarcted myocardial tissue in vivo, comprising the following steps performed in order:

administering an untargeted magnetic resonance (MR) contrast agent to a living patient;

waiting for a predetermined interval of time;

performing an MR study of the patient's heart; and identifying hyperenhanced myocardial tissue as infarcted myocardial tissue.

2. The method of claim 1, wherein the contrast agent is a chelate of Gadolinium.

3. The method of claim 1, wherein the interval of time is at least 10 minutes and at most 90 minutes.

4. The method of claim 1, wherein the MR study is carried out using a T1-weighted MR pulse sequence.

5. The method of claim 4, wherein the T1-weighted MR pulse sequence is of a magnetization driven spoiled gradient ("MD-SPGR") type.

6. The method of claim 4, wherein the T1-weighted MR pulse sequence is of an inversion-recovery fast low-angle shot ("IR-FLASH") type.

7. A method of differentiating normal myocardial tissue, injured myocardial tissue, and infarcted myocardial tissue using magnetic resonance imaging (MRI) of a living patient, comprising the following steps:

identifying infarcted myocardial tissue by administering an untargeted MR contrast agent to the patient, waiting a predetermined interval of time, performing a contrast-enhanced MR study of the patient's heart, and identifying hyperenhanced myocardial tissue;

identifying injured myocardial tissue by carrying out a cine MR study and identifying non-hyperenhanced myocardial tissue that exhibits abnormal motion; and identifying normal myocardial tissue by identifying myocardial tissue that exhibits neither hyperenhancement nor abnormal motion.

8. The method of claim 7, wherein the cine MR study is carried out after the administration of the MR contrast agent and before the contrast-enhanced MR study.

* * * * *

UNITED STATES PATENT AND TRADEMARK OFFICE
CERTIFICATE OF CORRECTION

PATENT NO. : 6,205,349 B1
DATED : March 20, 2001
INVENTOR(S) : Raymond Kim, Robert Judd, Jeffrey Bundy, Orlando Simonetti It is certified that error appears in the above-identified patent and that said Letters Patent is hereby corrected as shown below:

Column 1,
Line 5, after title of the invention, please insert the following paragraph in the above referenced patent:

-- The U.S. Government has a paid-up license in this invention and the right in limited circumstances to require the patent owner to license others on reasonable terms as provided for by the terms of Grant No. HL53411 awarded by The National Institutes of Health. --

Signed and Sealed this

Twenty-seventh Day of November, 2001

*Attest:*

*Attesting Officer*

NICHOLAS P. GODICI
*Acting Director of the United States Patent and Trademark Office*